(12) United States Patent
Bengtsson-Riveros et al.

(10) Patent No.: US 8,263,146 B2
(45) Date of Patent: Sep. 11, 2012

(54) CONSUMABLE PRODUCT CONTAINING PROBIOTICS

(75) Inventors: Annmarie Bengtsson-Riveros, St-Légier (CH); Johannes De Reu, Lienden (NL); Robert Dustan Wood, Quarante (FR); John Darbyshire, Tolochenaz (CH); Hermann Knauf, Lisieux (FR); Christoph Cavadini, Le Mont-Pelerin (CH)

(73) Assignee: Nestec S.A., Vevey (CH)

( * ) Notice: Subject to any disclaimer, the term of this patent is extended or adjusted under 35 U.S.C. 154(b) by 1914 days.

(21) Appl. No.: 10/468,645

(22) PCT Filed: Feb. 12, 2002

(86) PCT No.: PCT/EP02/01504
§ 371 (c)(1),
(2), (4) Date: Feb. 2, 2004

(87) PCT Pub. No.: WO02/065840
PCT Pub. Date: Aug. 29, 2002

(65) Prior Publication Data
US 2004/0115308 A1    Jun. 17, 2004

(30) Foreign Application Priority Data
Feb. 19, 2001  (EP) .................................. 01200593

(51) Int. Cl.
*A23L 1/00*  (2006.01)
(52) U.S. Cl. ........................ 426/61; 426/615; 426/618
(58) Field of Classification Search ................ 426/61, 426/615, 618, 619, 620, 621
See application file for complete search history.

(56) References Cited

U.S. PATENT DOCUMENTS

| | | | |
|---|---|---|---|
| 4,214,008 A | | 7/1980 | Groben et al. |
| 5,096,718 A | | 3/1992 | Ayres et al. |
| 5,968,569 A | * | 10/1999 | Cavadini et al. ............... 426/61 |
| 6,872,411 B1 | * | 3/2005 | Ross et al. ..................... 426/36 |
| 7,217,414 B2 | * | 5/2007 | Schiffrin et al. ........... 424/93.45 |

FOREIGN PATENT DOCUMENTS

| | | |
|---|---|---|
| DE | 33 00 122 A1 | 7/1984 |
| EP | 0 180 743 A1 | 5/1986 |
| EP | 0 298 605 | 1/1989 |
| EP | 0 656 751 | 6/1995 |
| EP | 1 148 064 | 10/2001 |
| GB | 831797 | 3/1960 |
| GB | 2 334 443 | 8/1999 |
| JP | 62-104552 | 5/1987 |
| JP | 06-038704 | 2/1994 |
| JP | 08-187071 | 7/1996 |
| JP | 08-187072 | 7/1996 |
| JP | 10-057031 | 3/1998 |
| JP | 10-191916 | 7/1998 |
| WO | WO 91/17672 | 11/1991 |
| WO | WO 92/12639 | 8/1992 |
| WO | 99/11147 | 3/1999 |
| WO | 99/47000 | 9/1999 |
| WO | 01/95745 | 12/2001 |
| WO | 98/10666 | 2/2009 |

OTHER PUBLICATIONS

Fennema, O.R., Food Chemistry, Second Edition, 1985, Marcel Dekker, Inc., New York, p. 57.*
R. Fuller article entitled "Probiotics in Man and Animals" *Journal of Applied Bacteriology*, 1989, 66, pp. 365-378.
Fujiwara, et al. "Proteinaceous Factor(s) in Culture Supernatant Fluids of *Bifidobacteria* Which Prevents the Binding of Enterotoxigenic *Escherichia coli* to Gangliotetraosylceramide," Applied and Environmental Microbiology, Feb. 1997, p. 506-512.
Gopal, et al. "In vitro adherence properties of *Lactobacillus rhamnosus* DR20 and *Bifidobacterium lactis* DR10 strains and their antagonistic activity against an enterotoxigenic *Escherichia coli*," International Journal of Food Microbiology 67 (2001) 207-216.
Granato, et al. "Cell Surface-Associated Lipoteichoic Acid Acts as an Adhesion Factor for Attachment of *Lactobacillus johnsonii* La1 to Human Enterocyte-Like Caco-2 Cells," Applied and Environmental Microbiology, Mar. 1999, p. 1071-1077.
Upreti, et al. "Isolation and Characterization of a Bacteriocin from a Homofermentative *Lactobacillus*," Antimicrobial Agents and Chemotherapy, Oct. 1973, p. 487-494.

* cited by examiner

*Primary Examiner* — Leslie Wong
(74) *Attorney, Agent, or Firm* — K&L Gates LLP

(57) ABSTRACT

The present invention relates to any kinds of consumable products enriched with probiotics and a method for obtaining them. After production of probiotic biomass, the probiotics are applied to the product. Also metabolites obtained from a fermentation product may be directly applied to a consumable product.

47 Claims, No Drawings

CONSUMABLE PRODUCT CONTAINING PROBIOTICS

This application is a national stage entry of PCT/EP02/01504, filed Feb. 12, 2002.

FIELD OF THE INVENTION

The present invention relates to a consumable product containing probiotics and to a process for obtaining it.

BACKGROUND OF THE INVENTION

Probiotic micro-organisms are micro-organisms which beneficially affect a host by improving its intestinal microbial balance. In general, it is believed that these bacteria inhibit or influence the growth and/or metabolism of pathogenic bacteria in the intestinal tract. It is also assumed that via probiotic micro-organisms the immune function of the host is activated. For this reason, there have been many different approaches to include probiotic micro-organisms into food-stuffs.

WO98/10666 (SOCIETE DES PRODUITS NESTLE S.A.) discloses a process for manufacturing a dehydrated food composition containing live probiotic acid bacteria, in which a food composition and a culture of probiotic lactic acid bacteria sensitive to oxygen are sprayed conjointly under a stream of hot air.

EP0862863 (SOCIETE DES PRODUITS NESTLE S.A.) discloses a dried, ready-to-eat cereal product comprising a gelatinised starch matrix which includes a coating or filling containing a probiotic microorganism.

U.S. Pat. No. 4,943,437 (AB MEDIPHARM) discloses a process for supply of biologically active materials to base food materials, in which the biologically active material is slurried in an inert carrier, where it is insoluble, to form a homogeneous suspension, after which the suspension is applied to the base material.

GB2205476 (UNILEVER) discloses a supported bacterial composition comprising an inert subdivided support, which is flour, and an aqueous suspension of viable microflora. This mixture is then dried and is suitable as inoculum of lactic acid bacteria for the preparation of sour-dough bread.

The incorporation of probiotic micro-organisms (hereinafter "probiotics") into foodstuff, however, entails a number of difficulties. One first goal to reach is to have an adequate number of cfu (colony forming unit) per day. If the concentration of the probiotics in the product does not exceed a certain threshold value, the beneficial effect is not provided. Hence, starting from the observation that that an effective dose is in the range of $10^9$ cfu per human per day, and, supposing, that the consumer has to take them within his/her daily intake, it is the objective to deliver this amount of cfu within one to three servings.

Hitherto, the approach has been to use probiotics that have been dried, either per se or together with a supporting substance. Hence, after fermentation in a suitable medium, the probiotics are usually concentrated, for example by centrifugation or filtration, and are then dried by spray-drying, fluidized-bed drying or freeze-drying. From the drying process, another, serious problem arises. That is, the probiotics sustain substantial loss in the range of 60, more frequently 90 to 99% of cfu depending on the applied technology, unless special measurements are taken. It goes without saying that these drying steps are very energy-expensive. But the high temperature drying process has other disadvantages. It may destroy or impair metabolites that are present in the probiotics them-selves or in the fermented medium where they were cultivated. Such metabolites may therefore lose their beneficial effects. The disadvantage of a concentration step, likewise, is the loss of metabolites that were present in the fermented medium.

The powder obtained by drying may then be applied to the desired food-product. According to the above cited EP0862863, for example, the dried probiotics are mixed with a liquid carrier substance, which is either oil, water or a protein digest. Then this substance is sprayed onto the food-product.

Due to the need of a relatively high number of cfu within a single meal and the high losses during drying, it is a problem to have a food-product with an effective number of cfu. A further problem, also addressed in the above cited references, is the long term stability of the probiotics on the food-product, i.e. the food-product with the probiotics has to be shelf stable at ambient temperature. Another concern is the viability of the probiotics in the stomach and the intestine. The probiotics must be sufficiently resistant to the acid environment in the stomach and to the bile acids in order to successfully colonize the intestine. Furthermore, the food-product comprising probiotics must be palatable to the consumer. There is a need to apply probiotics to a food-product without notably influencing its organoleptic properties.

It is indeed a problem to obtain only little or even no changes in flavor, appearance and texture of a finished product containing probiotics with respect to the same product without probiotics.

The present invention addresses the problems mentioned.

SUMMARY OF THE INVENTION

To this end, the present invention provides a consumable product comprising probiotics, wherein the probiotics were freshly applied to it.

In another aspect, the present invention provides a consumable product comprising metabolites produced by probiotics wherein the metabolites were comprised in a fermented medium that was separated from the probiotics cultivated therein.

Similarly, the process for obtaining a consumable product comprising probiotics, according to the present invention, comprises producing a fresh biomass of probiotics by fermentation in a liquid medium and directly applying the fresh biomass to the consumable product.

Moreover, in a fourth aspect, the process for obtaining a consumable product comprising metabolites produced by probiotics, according to the present invention, comprises cultivating probiotics in a liquid medium, separating the liquid medium from the probiotics and directly applying the liquid medium to the consumable product.

Contrary to reasonable expectation, it has indeed been found that biomass derived from a fermentation process can be directly and freshly applied to a consumable product without high temperature drying. By this way, a consumable product containing probiotics is obtained, which has an excellent storage stability and which has an appearance and organoleptic properties similar to the appearance and the organoleptic properties of a similar consumable product not containing probiotics.

Furthermore, the consumable product, if consumed in the expected or reasonable amount, contains an amount of cfu that is sufficient to exert a beneficial effect.

Advantageously, metabolites and micro-organisms are no longer lost due to drying process and concentration.

DETAILED DESCRIPTION OF THE INVENTION

Throughout the present description the expression "consumable product" means a product which is consumable by humans and/or by pets such as dogs or cats, for example.

With respect to the present invention, "fresh probiotics" or "freshly applied biomass" refers to probiotics that, after the fermentation process, are not dried, for example by spray-, fluidized bed or freeze-drying. However, "fresh probiotics" is not intended to be understood as biomass that is applied within a certain time limit to the consumable product. It is easily possible to store the "fresh biomass" for a certain time without loss. If the biomass can also be frozen for a certain time and thawed out without substantial loss, this is still considered as fresh. It is also possible to add to the "fresh biomass" protective agents known to improve the survival of, for example, lactic acid bacteria during the application process, for example during spraying onto the consumable product, during storage of the product and also during the passing of the consumable product through the digestive tracts. WO 98/10666 mentions some of the substances with such effects and also gives an extensive list of prior art that is concerned with the improvement of the survival of probiotic microorganisms. Despite of such additives, the biomass can be regarded as "fresh biomass", because there is no high-temperature drying process.

For the purpose of the present invention, the term "probiotics", "probiotic micro-organism" or probiotic biomass is understood to include any micro-organisms, cell content or metabolites from micro-organisms, having beneficial effects to its host. Therefore, yeasts, moulds and bacteria may be included. EP 0862863 lists some examples for probiotics presently known. For example, strains of *Lactobacillus johnsonii* (CNCM I-1225), *Bifidobacterium lactis* (DSM20215), *Streptococcus thermophilus* (TH4, Chr. Hansen, D K), or *Lactobacillus paracasei* (CNCM I-2116) may be used. A selection of different probiotic strains is offered by Christian Hansen BioSystems A/S (CHL), 10-12 Boge Allé, P.O Box 407, DK-2970 Horsholm, Denmark.

For the purpose of the present invention, the term "probiotics" furthermore is intended to include the metabolites generated by the micro-organisms during a fermentation process, if they are not separately indicated. These metabolites may be released to the medium of fermentation or they may be stored within the micro-organism. It may well be, that such metabolites are responsible for part or all of the beneficial effects of a particular probiotic micro-organism.

Surprisingly, it has been found that probiotics need not necessarily be concentrated and don't need to be dried at high temperatures but can be directly and freshly applied to a food product. The present invention has therefore also the big advantage, that there isn't a high temperature treatment that may impair or even destroy the effectivity of metabolites produced by the probiotics. The fact that the concentration step can be omitted has the advantage that effective metabolites present in the fermented medium are not lost, for example by filtration.

Thus, it has surprisingly been found that it is indeed possible to provide a consumable product containing probiotics which has an excellent storage stability and which has an appearance and organoleptic properties similar to the appearance and the organoleptic properties of a similar consumable product not containing probiotics. Contrary to all expectations, it has been found that fresh and direct application of probiotic biomass to a consumable product causes no or only very small changes in flavour, appearance and texture of the finished product containing probiotics.

Contrary to current thinking in probiotics-food-technology, it is also possible to spray the fresh biomass onto a dried food-product, for example a breakfast-cereal, without need of a high temperature drying process before, during or after application of the biomass. Within the meaning of the present invention, only a relatively small amount of liquid or slurry derived from a fermentation process has to be sprayed on to the dried food product. Preferably, the fermentation is continued until a relatively high concentration of cfu is obtained. The food-product will absorb most of the water without substantial increase of the water activity of the respective food-product. For this reason, it is also not necessary to subject the consumable product comprising probiotics to a further process of drying or other treatment, as suggested by the literature. Interestingly, up to this date there has always been the problem to add a lot of probiotics and then to dry the end-product. Only few cfu normally survive the drying process. In order to compensate for this loss, a high abundance of probiotics, for example in a carrier as water, had to be applied. This in turn made a drying process necessary, especially in a product that was intended to be dry at the end. In contrast to this, the present invention avoids a destructive drying process and therefore it is not necesary any more to apply probiotics in high abundance to the consumable product. As a consequence, a relatively small amount of slurry or liquid from the fermentor comprising probiotics has to be applied to the consumable product. Of course, also according to the present invention, a comparatively slight abundance of probiotics still may be applied to the consumable product in order to compensate for the inevitable losses during storage as well as passage through the digestive tract of the product.

Surprisingly, shelf life studies have revealed that the viability of the probiotics on the food products obtained by direct biomass application is very high. Depending on the probiotic organism used, the probiotics retain their activity up to 365 days without substantial loss.

Furthermore, it has surprisingly been found that probiotics applied to a food product show, depending on the species and strain of the probiotic organism, sufficient resistance to the environment of the stomach and the gastric and bile acids (in vitro tests).

According to the consumable product provided by present invention, at least one protective agent may be added to the probiotics prior to their application to the consumable product, for example.

The probiotics according to the invention may be obtained by fermentation and they may be stored after fermentation and before application to the consumable product for a time and at a temperature that prevents substantial loss of probiotic cfu, for example. It is clear that the biomass, after termination of the fermentation or cultivation, may be stored for a certain time. In experiments, the biomass of different probiotics was stored for 4 days at 5° C. without detectable loss. Furthermore, also the resistance to gastric or bile acid (in vitro tests) was not influenced by storage time.

For carrying out the invention, the probiotics may be fermented until a final concentration of $10^6$ to $5\times10^{10}$, preferably $10^7$ to $3\times10^{10}$, more preferably $1.5\times10^7$ to $10^{10}$, even more preferably $10^8$ to $9.5\times10^9$, in particular 2 to $9\times10^9$ cfu per ml of fermented medium is achieved, for example.

It is possible, that the probiotics to be applied to the food product are concentrated to a final concentration of $10^7$ to $10^{12}$, preferably $10^8$ to $5\times10^{11}$, more preferably $1.5\times10^8$ to $10^{11}$, even more preferably $10^9$ to $5\times10^{10}$ cfu per ml of fermented medium, for example.

For the fermentation, any probiotic micro-organism may be used.

According to the invention, a probiotic strain or strains may be selected from a group comprising yeasts, preferably the genus *Saccharomyces*, moulds, preferably the genus *Aspergillus*, bacteria, preferably the genus *Lactobacillus, Bifidobacterium, Streptococcus, Enterococcus*, and a mixture thereof. For example, strains from the species *Lactobacillus johnsonii, Bifidobacterium lactis, Streptococcus thermophilus*, or, *Lactobacillus paracasei* may be used. For example, if bacterial probiotics are to be produced, strains may be selected from the geni *Lactobacillus, Streptococcus, Bifidobacterium, Bacteroides, Clostridium, Fusobacterium, Nelissococcus, Propionibacterium, Enterococcus, Lactococcus, Staphylococcus, Peptostreptococcus, Bacillus, Pediococcus, Micrococcus, Leuconostoc, Weissella, Aerococcus, Oenococcus*.

Hence, in an embodiment of the present invention, a probiotic strain or strains may be selected from a group comprising *Bifidobacterium lactis* (DSM20215), *Lactobacillus johnsonii* (I-1225 CNCM), *Lactobacillus paracasei* (I-2116 CNCM), *Streptococcus thermophilus* (TH4, Chr. Hansen, D K), mixtures thereof, and a mixture also comprising other probiotic micro-organisms, for example.

According to the present invention, the percentage of fresh biomass of probiotics added to the consumable product may be 0.05 to 4%, preferably 0.1 to 1.5%, most preferably 0.2 to 1% by weight of the consumable product, for example.

Accordingly, the final concentration of the probiotics applied to the consumable product may be $10^6$ to $10^9$, more preferably, $10^7$ to $10^8$, most preferably 2 to $8\times10^7$ cfu/g with respect to the total weight of the consumable product, for example.

According to the consumable product comprising metabolites produced by probiotics, the fermented medium may have been directly applied to the consumable product.

According to the process of the present invention, the fermentation may be kept ongoing until a final concentration of $10^6$ to $5\times10^{10}$, preferably $10^7$ to $3\times10^{10}$, more preferably $1.5\times10^7$ to $10^{10}$, even more preferably $10^8$ to $9.5\times10^9$, in particular 2 to $9\times10^9$ probiotic cfu per ml of fermented medium is achieved, for example.

According to the desired concentration and water activity (Aw) of the final consumable product, the process of the present invention may comprise, before applying the fresh biomass to a consumable product, concentrating the biomass to a final concentration of $10^7$ to $10^{12}$, preferably $10^8$ to $5\times10^{11}$, more preferably $1.5\times10^8$ to $10^{11}$, even more preferably $10^9$ to $5\times10^{10}$ cfu per ml of fermented medium, for example.

For example, the Aw of the consumable product at the beginning and/or during shelf life is below 0.5. Preferably, it is below 0.4 and more preferably it is smaller than 0.3. Most preferably, the Aw of the consumable product is below 0.2. For example, the Aw is in the range of 0.005 to 0.3, or 0.01 to 0.15 during the shelf life of the consumable product.

The Aw that the product may have depends on the capability of the straim to survive the specific conditions, which may be different from strain to strain.

Preferably, the consumable product has a packaging that substantially limits the water uptake from the environment. Hence, the $O_2$ permeation rate of the packaging of the consumable product is preferably below 4.2 ml/m² d, preferably below 3.8 ml/m² d. Likewise, the water vapor transmission rate (WVTR) of the packaging of the consumable product is preferably below 3.5 g/m² d, more preferably below 3 g/m² d. The skilled person is able to select the material with such properties. For example, the packaging may comprise co-extruded cross-linked oriented low density polyethylene (LDPE). The bags may be hermetically sealed, for example heat-sealed.

The purpose of the packaging as characterized above is to maintain the preferred Aw values during the shelf life of the consumable product. The shelf life of the product may be up to 6 months, preferably up to 12 months, more preferably up to 18 months and most preferably up to two years.

In another embodiment, the process may further comprise, after fermentation, storing the fresh biomass for a time and at a temperature that prevents substantial loss of probiotic cfu, for example.

In yet another embodiment of the present invention the process may further comprise, before, during or after producing fresh biomass of probiotics, adding of at least one protective agent to the medium of fermentation or to the fresh probiotic biomass, for example.

The fermentation process according to the present invention may be kept ongoing for 6 hours to 3 days, preferably 6 to 20 hours, more preferably 7 to 17 hours, depending on the strain of probiotic micro-organism used, for example.

According to the process according to present invention, the same strain or strains may be used as described above with respect to a consumable product comprising probiotics, for example.

It is possible that the percentage of fresh biomass of probiotics added to the consumable product may be 0.05 to 4%, preferably 0.1 to 1.5%, most preferably 0.2 to 1% by weight of the consumable product, for example.

Therefore, according to an embodiment of the present invention, the final concentration of the probiotics applied to the consumable product may be $10^6$ to $10^9$, more preferably, $10^7$ to $10^8$, most preferably 2 to $8\times10^7$, in particular $5\times10^7$ cfu/g of the consumable product.

It is possible, although not necessary, that the biomass freshly derived from the fermenting process be concentrated. For example, such concentration can be achieved by centrifugation or filtration. The level of concentration allows dosing accurately the amount of cfu per gram of consumable products. The concentration may also take into account the subsequent loss of cfu during shelf-life of the food-product or during passage of the digestive tract. A high-temperature drying process can be avoided by spraying or otherwise applying not concentrated or relatively little concentrated biomass to the consumable product, so that the water activity of the overall product does not decisively increase. A high temperature drying process is not necessary due to "absorbtive drying"; the already dried food product absorbs rapidly the water accompanied by and contained in the probiotic biomass. The exposure to room temperature during the process of application is sufficient to prevent a decisive increase of water activity of the final product.

In case that the biomass was concentrated, the supernatant obtained thereby need not be discarded. The medium after the fermentation with probiotics usually contains metabolites having similar beneficial effects as the probiotics themselves. Therefore, the supernatant medium may, after concentration of the biomass, also be applied to a consumable product.

For carrying out the process according to the present invention, all kind of starting consumable products may be used. Food and beverages for humans as well as pet food may be enriched by probiotics. Of course, also nutritional formulas for each and every purpose may be supplied with probiotics. There exists a huge variety of nutritional formulas, for example for sportsmen or athletes, for people with special nutritional needs such as people allergic to certain natural food components or people with gastrointestinal disorders and so forth. For example, also chocolate or other sweet products may be supplied with probiotics. In fact, all kind of extruded or cooked or otherwise prepared food products may be furnished with probiotics. For example, dried products may be used, such as dried pet food or other dried food products, like for example powders, flours, milk or cereal powders or cereal flakes. Probiotics may be used to be applied to all kind of breakfast cereals, for example. Also components, ingredients or starting materials of consumable products may be sprayed with probiotics. For example, particles of one or more cooked cereal bases mainly comprising amylaceous materials are suitable. Particles of cooked cereal bases may be any of those known to the man skilled in the art as flaked cereals, shredded whole grains, extruded and other shredded cereals, rolled cereals, gun puffed grains, oven-puffed cereals, extruded gun-puffed cereals, flakes and/or cooked-extruded cereals, extruded expanded cereals, baked breakfast cereals, compressed-flake biscuits, for example. Cereal flakes may be prepared by cooking cereal grits or grains with a liquor, forming pellets out of the cooked mass thus obtained, rolling, toasting and possibly coating them with sugar, for example.

The production of probiotic biomass is a process that is well known in the art. Usually, specially equipped fermentation units or tanks are used. Although, in principle even a sterile tank comprising medium may be suitable to cultivate micro-organisms. According to the particular preferrences of a certain probiotic strain, the medium composition is chosen. An optimal medium composition for a particular probiotic strain is in general furnished together with the probiotic starter organisms from the supplier. After the fermentation is completed, the biomass may be directly applied to the consumable product. It's also possible to store it for a certain time without altering its suitability for application to a consumable product. Especially if a transport to the production place of the consumable product is mandatory, the probiotic biomass may also be transitionally frozen, in order to prevent loss of probiotic cfu.

Before applying the biomass to a consumable product, the biomass may be concentrated. The concentration step, albeit not mandatory, may be appropriate if even a slight increase in water content of the end product has to be avoided, for example. Furthermore, a concentration may also be conducted if the final concentration of probiotic on the product has to be particularly high, be it because only a small, single serving of the consumable product has to comprise a sufficient number of cfu, be it for other reasons. The concentration-process is also well known in the art. In general, the method of choice is filtration or centrifugation.

Lastly, the probiotic biomass, whether concentrated or not, is applied to the consumable product. This application may be conducted according to the general rules of coating of food-products. For example, the application of biomass may take place as the product is transported on a conveyor or, alternatively, in a coating drum. Numerous options are available in the design of a spray system, from a crimped pipe to a spinning disk. Some products may be suitable for a treatment in a coating drum, for example in a rotating drum. The coating drum may serve as both a blender and a mechanism for exposing the cereal to the spray. The biomass may be sprayed on top of the rotating cereals using commercial two-phase (air/liquid) spraying nozzles. In general, for dryed products as breakfast cereals, for example, the same spraying system as for coating with a vitamin solution may be used. These techniques are well known in the art.

Depending on particularities and preferences, the food product now comprising probiotics may be exposed to ambient or elevated temperature, in a way that no substantial loss of cfu is taken into account. It is also possible to freeze the food product, depending on its nature or purpose of the final food product. Of course, other further treatments or processing of the consumable product may occur, depending on the end-product or the purpose of the consumable product. An example would be the aeration of the final product with an inert gas or gas mixture like $N_2$ or $N_2/CO_2$.

The process and the product according to the present invention are described in greater detail in the examples presented below by way of illustration.

EXAMPLES

The strains used for the examples are the following:
*Bifidobacterium lactis**: DSM20215 (German Culture Collection)
*Streptococcus thermophilus* (TH4)*
*Lactobacillus johnsonii*: I-1225 (CNCM)
*Lactobacillus paracasei*: I-2116 (CNCM)

\* obtained from Christian Hansen BioSystems A/S (CHL), 10-12 Boge Allé, P.O Box 407, DK-2970 Horsholm, Denmark.

For the experiments, a junior cereal product, breakfast cereal flakes, a cereal/milk snack and an infant cereal powder were used. Table 1 below shows the compositions and production method of these products.

TABLE 1

Composition and production of consumable products referred to in the examples

| Product | Product type | Composition | Density g/l |
|---|---|---|---|
| junior cereal product | Extruded cereal rings with sugar/honey coating | Cereals (wheat, oats and barley), sugar, honey, maltodextrin, vitamins and minerals | 115 |
| breakfast cereal flakes | Traditionally cooked wheat flakes with light sugar coating | Whole wheat, sugar, refiners syrup, malt, salt, honey, glucose, vitamins and minerals | 135 |
| Cereal/ milk snack | Extruded fruit shaped cereals with high milk content | Wheat flour, milk powder, sugar, banana concentrate, maltose, starch, salt, vitamins and minerals, aromas | 130 |
| infant cereal powder | Wheat based infant cereal formula | Wheat flour, sugar, lecithin, vanillin, vitamins and minerals | 315 |

Example 1

*Bifidobacterium lactis* Biomass Applied to Different Products

*Bifidobacterium lactis* was fermented and then concentrated by centrifugation. Details of the fermentation are given in tables 2 and 3 below. Standard protective agents were added to the concentrate. This biomass was added in bench-scale to different commercial available cereal products (see table 1 above).

For the bench-scale application 1.5-2 kg of cereal product was put into a rotating batch coating drum and the biomass was sprayed on top of the rotating cereals using a commercial spray pistol with a two-phase (air/liquid) nozzle. The pistol containing the biomass was carefully weighed before and after spraying to estimate the exact amount of biomass applied on the cereal. In all cases 0.5% of the total cereal amount was added.

TABLE 2

Medium composition for *Bifidobacterium lactis* (example 1).
Medium composition

| Ingredient | Quantity (g/l) |
| --- | --- |
| Whey permeate | 14 |
| Dextrose | 25 |
| Anti foaming agent | 1 |
| Whey protein hydrolysate | 5 |
| Yeast extract | 28 |
| Meat peptone | 4 |
| Fructose | 14 |
| Buffer salts | 10 |
| Milk powder | 0.8 |

TABLE 3

Fermentation parameters for *Bifidobacterium lactis* (example 1).

| Fermentation scale | 200 l media |
| --- | --- |
| Temperature | 37° C. |
| Incubation time | 14 hours |
| Viable counts at end of fermentation | $1 \times 10^{10}$ cfu/ml |
| Viable counts after centrifugation and addition of protective agents | $9 \times 10^{10}$ |

TABLE 4

Results of application trials

| Product | Viable counts (cfu/g) on product | $A_w$ on finished product |
| --- | --- | --- |
| Junior cereal product | $1.5 \times 10^8$ | 0.15 |
| Breakfast cereal flakes | $8.8 \times 10^7$ | 0.3 |
| Cereal/Milk snack | $1.5 \times 10^8$ | 0.1 |
| Infant cereal powder | $1.1 \times 10^8$ | 0.3 |

As table 4 unarguably shows, high viable counts per g of consumable product are obtained. The water activity remains in a, for storing purposes, acceptable frame.

Example 2

*Bifidobacterium lactis, Lactobacillus johnsonii, Lactobacillus paracasei, Streptococcus thermophilus* Biomass Applied to a Junior Cereal Product Different strains were fermented (fermentation details are given in tables 5 to 12) and then concentrated by centrifugation. Standard protective agents were added to the concentrate. 0.5% by weight total product of the different biomass were added in bench-scale to a commercially available junior cereal product. (Same method as for example 1)

TABLE 5

Medium composition for *Bifidobacterium lactis* (example 2).
Medium composition

| Ingredient | Quantity (g/l) |
| --- | --- |
| Whey permeate | 14 |
| Dextrose | 25 |
| Anti foaming agent | 1 |
| Milk protein hydrolysate | 5 |
| Yeast extract | 28 |
| Meat peptone | 4 |
| Fructose | 14 |
| Buffer salts | 10 |
| Milk powder | 0.8 |

TABLE 6

Fermentation parameters for *Bifidobacterium lactis* (example 2).

| Fermentation scale | 200 l media |
| --- | --- |
| Temperature | 37° C. |
| Incubation time | 14 hours |
| Viable counts at end of fermentation | $1 \times 10^{10}$ cfu/ml |
| Viable counts after centrifugation and addition of protective agents | $9 \times 10^{10}$ cfu/ml |

TABLE 7

Medium composition for *Lactobacillus johnsonii* (example 2).

| Ingredient | Quantity (g/l) |
| --- | --- |
| Whey permeate | 15 |
| Dextrose | 15 |
| Anti foaming agent | 1 |
| Whey protein hydrolysate | 5 |
| Yeast extract | 30 |
| Meat peptone | 5 |
| Fructose | 15 |
| Buffer salts | 10 |
| Milk powder | 10 |

TABLE 8

Fermentation parameters for *Lactobacillus johnsonii* (example 2).

| Fermentation scale | 2000 l media |
| --- | --- |
| Temperature | 40° C. |
| Incubation time | 14 hours |
| Viable counts at end of fermentation | $7 \times 10^9$ cfu/ml |
| Viable counts after centrifugation and addition of protective agents | $5 \times 10^{10}$ cfu/ml |

TABLE 9

Medium composition for *Streptococcus thermophilus* (example 2).

| Ingredient | Quantity (g/l) |
| --- | --- |
| Whey permeate | 50 |
| Anti foaming agent | 1 |
| Whey protein hydrolysate | 5 |
| Yeast extract | 20 |

TABLE 9-continued

Medium composition for *Streptococcus thermophilus* (example 2).

| Ingredient | Quantity (g/l) |
|---|---|
| Meat peptone | 5 |
| Fructose | 5 |
| Buffer salts | 5 |

TABLE 10

Fermentation parameters for *Streptococcus thermophilus* (example 2).

| | |
|---|---|
| Fermentation scale | 200 l media |
| Temperature | 40° C. |
| Incubation time | 6 hours |
| Viable counts at end of fermentation | $2 \times 10^9$ cfu/ml |
| Viable counts after centrifugation and addition of protective agents | $4 \times 10^{10}$ cfu/ml |

TABLE 11

Medium composition for *Lactobacillus paracasei* (example 2).

| Ingredient | Quantity (g/l) |
|---|---|
| Soya peptone | 10 |
| Anti foaming agent | 1 |
| Yeast extract | 15 |
| Fructose | 30 |
| Buffer salts | 7.5 |

TABLE 12

Fermentation parameters for for *Lactobacillus paracasei* (example 2).

| | |
|---|---|
| Fermentation scale | 200 l media |
| Temperature | 37° C. |
| Incubation time | 17 hours |
| Viable counts at end of fermentation | $9 \times 10^9$ cfu/ml |
| Viable counts after centrifugation and addition of protective agents | $9 \times 10^{10}$ cfu/ml |

TABLE 13

Results of application trials on a junior cereal product.

| Biomass | Viable counts (cfu/g) on product | $A_w$ on finished product |
|---|---|---|
| *Bifidobacterium lactis* | $1.5 \times 10^8$ | 0.15 |
| *Lactobacillus johnsonii* | $2.5 \times 10^8$ | <0.1 |
| *Streptococcus thermophilus* | $2.8 \times 10^8$ | <0.1 |
| *Lactobacillus paracasei* | $2 \times 10^8$ | <0.1 |

Also other strains applied to the junior cereal product revealed sufficient viable counts and a low final water activity.

Example 3

Shelf Life Data on a Junior Cereal Product with *Lactobacillus johnsonii*

*Lactobacillus johnsonii* was fermented and then concentrated by centrifugation (for fermentation details see tables 14 and 15). Standard protective agents were added to the concentrate. This biomass was added in pilot-scale to a junior cereal product.

For the pilot-scale application 100 kg/h of the junior cereal product was introduced to an continuous enrobing drum. 0.5 kg/h of *Lactobacillus johnsonii* biomass was sprayed on top of the cereal with a series of two-phase (air/liquid) nozzles.

Finished product was packed in aluminium liners and submitted to shelf life study at 20° C. (results see table 16).

TABLE 14

Medium composition for *Lactobacillus johnsonii* (example 3)

| Ingredient | Quantity (g/l) |
|---|---|
| Whey permeate | 15 |
| Dextrose | 15 |
| Anti foaming agent | 1 |
| Whey protein hydrolysate | 5 |
| Yeast extract | 30 |
| Meat peptone | 5 |
| Fructose | 15 |
| Buffer salts | 10 |
| Milk powder | 10 |

TABLE 15

Fermentation parameters for *Lactobacillus johnsonii* (example 3).

| | |
|---|---|
| Fermentation scale | 2000 l media |
| Temperature | 40° C. |
| Incubation time | 14 hours |
| Viable counts at end of fermentation | $3 \times 10^9$ cfu/ml |
| Viable counts after centrifugation and addition of protective agents | $1 \times 10^{10}$ cfu/ml |

TABLE 16

Results of application and shelf life on a junior cereal product.

| Days at 20° C. | Viable counts (cfu/g) on product | $A_w$ on finished product |
|---|---|---|
| Start | $1.3 \times 10^8$ | <0.1 |
| 90 | $1.6 \times 10^8$ | <0.1 |
| 180 | $1.1 \times 10^8$ | <0.1 |
| 270 | $1.3 \times 10^8$ | <0.1 |
| 365 | $9.5 \times 10^7$ | <0.1 |

The shelf-life study reveals that storage for up to one year does not substantially reduce the number of cfu on the product.

Example 4

Addition of Concentrated and Non-concentrated *Bifidobacterium lactis*, Direct and After 4 Days Storage of Biomass to a Junior Cereal Product

*Bifidobacterium lactis* was fermented (details are given in tables 17 and 18), a part of the biomass was used directly and a second part was concentrated by centrifugation with addition of standard protective agents. Both biomasses were added bench-scale to a junior cereal product. A second serie of trials was conducted with the same biomasses stored at 5° C. for 4 days prior to application.

For the bench-scale application 2 kg of cereal product was put into a rotating batch coating drum and the biomass was sprayed on top of the rotating cereals using a commercial spray pistol with a two-phase (air/liquid) nozzle. In all cases 0.5% of the total cereal amount was added. In one case the biomass was used directly after fermentation and in the other case it was concentrated and then the same steps were repeated with biomasses stored for 4 days (5° C.) prior to application.

The finished products were also analysed In vitro for gastric tract resistance.

TABLE 17

Medium composition for *Bifidobacterium lactis* (example 4).

| Ingredient | Quantity (g/l) |
| --- | --- |
| Whey permeate | 14 |
| Dextrose | 25 |
| Anti foaming agent | 1 |
| Whey protein hydrolysate | 5 |
| Yeast extract | 28 |
| Meat peptone | 4 |
| Fructose | 14 |
| Buffer salts | 10 |
| Milk powder | 0.8 |

TABLE 18

Fermentation parameters for *Bifidobacterium lactis* (example 4).

| | |
| --- | --- |
| Fermentation scale | 200 l media |
| Temperature | 37° C. |
| Incubation time | 14 hours |
| Viable counts at end of fermentation | $9 \times 10^9$ cfu/ml |
| Viable counts taken from fermentation and stored for 4 days at 5° C. | $5 \times 10^9$ cfu/ml |
| Viable counts after centrifugation and addition of protective agents | $8 \times 10^{10}$ cfu/ml |
| Viable counts after centrifugation and addition of protective agents and stored 4 days at 5° C. | $6 \times 10^{10}$ cfu/ml |

TABLE 19

Results of application trials on a junior cereal product.

| *Bifidobacterium lactis* Biomass | Viable counts (cfu/g) on product | Total log losses in gastro-intestinal tract (In vitro) |
| --- | --- | --- |
| Non-concentrated | $3 \times 10^7$ | 0.4 |
| Non-concentrated stored | $2 \times 10^7$ | 0.4 |
| Concentrated | $4 \times 10^8$ | 0.2 |
| Concentrated stored | $7 \times 10^8$ | 0.3 |

As table 19 shows, the losses in a simulated intestinal environment are in an acceptable range.

The invention claimed is:

1. A dried consumable product comprising fresh-probiotics, wherein the fresh probiotics are directly added to the dried consumable product, and wherein the water activity of the dried consumable product after the fresh probiotics are added is less than about 0.3.

2. The consumable product according to claim 1, wherein at least one protective agent has been added to the fresh probiotics prior to an application of the fresh probiotic to the consumable product.

3. The consumable product according to claim 1, wherein the fresh probiotics were obtained by fermentation and the fresh probiotics were stored after fermentation and before application to the consumable product for a time and at a temperature that prevents substantial loss of probiotic colony forming units (cfu).

4. The consumable product according to claim 1, wherein the fresh probiotics were fermented until a final concentration of $10^6$ to $5 \times 10^{10}$ cfu per ml of fermented medium was achieved.

5. The consumable product according to claim 1, wherein the fresh probiotics were concentrated to a final concentration of $10^7$ to $10^{12}$ cfu per ml of fermented medium.

6. The consumable product according to claim 1, wherein the fresh probiotic is from at least one strain selected from the group consisting of yeasts, moulds, and bacteria.

7. The consumable product according to claim 1, wherein the fresh probiotic is from at least one strain selected from the group consisting of *Bifidobacterium lactis* (DSM20215), *Lactobacillus johnsonii* (I-1225 CNCM), *Lactobacillus paracasei* (I-2116 CNCM), and *Streptococcus thermophilus* (TH4, Chr. Hansen, D K).

8. The consumable product according to claim 1, wherein the percentage of fresh biomass of fresh probiotics added to the consumable product is 0.05 to 4%, by weight of the consumable product.

9. The consumable product according to claim 1, wherein the final concentration of the fresh probiotics applied to the consumable product is $10^6$ to $10^9$ cfu/g with respect to the total weight of the consumable product.

10. A dried consumable product comprising fresh metabolites produced by probiotics wherein the fresh metabolites are comprised in a fermented medium that was separated from the probiotics cultivated therein, wherein the fermented medium is directly applied to the dried consumable product, and wherein the water activity of the dried consumable product after the fermented medium is applied is less than about 0.3.

11. A method for producing a dried consumable product comprising fresh probiotics, comprising the steps of producing a biomass of fresh probiotics by fermentation in a liquid medium and directly applying the biomass of fresh probiotics to the dried consumable product, wherein the water activity of the dried consumable product after the biomass of fresh probiotics is applied is less than about 0.3.

12. The method according to claim 11 wherein the fermentation is continued until a final concentration of $10^6$ to $5 \times 10^{10}$ probiotic cfu per ml of fermented medium is achieved.

13. The method according to claim 11, which further comprises the steps of, before applying the fresh biomass to a consumable product, concentrating the biomass to a final concentration of $10^7$ to $10^{12}$ cfu per ml of fermented medium.

14. The method according to claim 11, wherein the process further comprises the steps of, after fermentation, storing the fresh biomass for a time and at a temperature that prevents substantial loss of probiotic cfu.

15. The method according to claim 11, wherein the process further comprises the steps of, before, during or after producing the fresh biomass of probiotics, adding at least one protective agent to the medium of fermentation or to the fresh probiotic biomass.

16. The method according to claim 11, wherein the fermentation is continued for 6 hours to 3 days, depending on the strain of probiotic micro-organism used.

17. The method according to claim 11, wherein the probiotic is at least one strain selected from a group comprising yeasts, moulds, and bacteria.

18. The method according to claim 11, wherein the percentage of fresh biomass of probiotics added to the consumable product is 0.05 to 4% by weight of the consumable product.

19. The method according to claim 11, wherein the final concentration of the probiotics applied to the consumable product is $10^6$ to $10^9$ cfu/g of the consumable product.

20. The method according to claim 11, wherein the probiotic is at least one strain selected from the group consisting of *Bifidobacterium lactis* (DSM20215), *Lactobacillus johnsonii* (I-1225 CNCM), *Lactobacillus paracasei* (I-2116 CNCM), and *Streptococcus thermophilus* (TH4, Chr. Hansen, D K).

21. A method for producing a dried consumable product comprising fresh metabolites produced by probiotics, which comprises the steps of cultivating probiotics in a liquid medium, separating the liquid medium from the probiotics and directly applying the liquid medium to the dried consumable product, wherein the water activity of the dried consumable product after the liquid medium is applied is less than about 0.3.

22. The consumable product according to claim 1, wherein the fresh probiotics were fermented until a final concentration of $10^7$ to $3 \times 10^{10}$ cfu per ml of fermented medium was achieved.

23. The consumable product according to claim 1, wherein the fresh probiotics were fermented until a final concentration of $1.5 \times 10^7$ to $10^{10}$ cfu per ml of fermented medium was achieved.

24. The consumable product according to claim 1, wherein the fresh probiotics were fermented until a final concentration of $10^8$ to $9.5 \times 10^{10}$ cfu per ml of fermented medium was achieved.

25. The consumable product according to claim 1, wherein the fresh probiotics were fermented until a final concentration of 2 to $9 \times 10^9$ cfu per ml of fermented medium was achieved.

26. The consumable product according to claim 1, wherein the fresh probiotics were concentrated to a final concentration of $10^8$ to $5 \times 10^{11}$ cfu per ml of fermented medium.

27. The consumable product according to claim 1, wherein the fresh probiotics were concentrated to a final concentration of $1.5 \times 10^8$ to $10^{11}$ cfu per ml of fermented medium.

28. The consumable product according to claim 1, wherein the fresh probiotics were concentrated to a final concentration of $10^9$ to $5 \times 10^{10}$ cfu per ml of fermented medium.

29. The consumable product according to claim 1, wherein the fresh probiotic is from at least one strain selected from the group consisting of the genus *Saccharomyces*, the genus *Aspergillus*, bacteria, the geni *Lactobacillus, Bifidobacterium, Streptococcus*, and *Enterococcus*.

30. The consumable product according to claim 1, wherein the percentage of fresh biomass of fresh probiotics added to the consumable product is 0.1 to 1.5%, by weight of the consumable product.

31. The consumable product according to claim 1, wherein the percentage of fresh biomass of fresh probiotics added to the consumable product is 0.2 to 1%, by weight of the consumable product.

32. The consumable product according to claim 1, wherein the final concentration of the fresh probiotics applied to the consumable product is $10^7$ to $10^8$ cfu/g with respect to the total weight of the consumable product.

33. The consumable product according to claim 1, wherein the final concentration of the fresh probiotics applied to the consumable product is 2 to $8 \times 10^7$ cfu/g with respect to the total weight of the consumable product.

34. The method according to claim 11 wherein the fermentation is continued until a final concentration of $10^7$ to $3 \times 10^{10}$ probiotic cfu per ml of fermented medium is achieved.

35. The method according to claim 11 wherein the fermentation is continued until a final concentration of $1.5 \times 10^7$ to $10^{10}$ probiotic cfu per ml of fermented medium is achieved.

36. The method according to claim 11 wherein the fermentation is continued until a final concentration of $10^8$ to $9.5 \times 10^9$ probiotic cfu per ml of fermented medium is achieved.

37. The method according to claim 11 wherein the fermentation is continued until a final concentration of 2 to $9 \times 10^9$ probiotic cfu per ml of fermented medium is achieved.

38. The method according to claim 11, which further comprises the steps of, before applying the fresh biomass to a consumable product, concentrating the biomass to a final concentration of cfu per ml of fermented medium $10^8$ to $5 \times 10^{11}$.

39. The method according to claim 11, which further comprises the steps of, before applying the fresh biomass to a consumable product, concentrating the biomass to a final concentration of cfu per ml of fermented medium $1.5 \times 10^8$ to $10^{11}$.

40. The method according to claim 11, which further comprises the steps of, before applying the fresh biomass to a consumable product, concentrating the biomass to a final concentration of cfu per ml of fermented medium $10^9$ to $5 \times 10^{10}$.

41. The method according to claim 11, wherein the fermentation is continued for preferably 6 to 20 hours.

42. The method according to claim 11, wherein the fermentation is continued for preferably 7 to 17 hours.

43. The method according to claim 11, wherein the fresh probiotic is from at least one strain selected from the group consisting of the genus *Saccharomyces*, the genus *Aspergillus*, bacteria, the geni *Lactobacillus, Bifidobacterium, Streptococcus*, and *Enterococcus*.

44. The method according to claim 11, wherein the percentage of fresh biomass of fresh probiotics added to the consumable product is 0.1 to 1.5%, by weight of the consumable product.

45. The method according to claim 11, wherein the percentage of fresh biomass of fresh probiotics added to the consumable product is 0.2 to 1%, by weight of the consumable product.

46. The method according to claim 11, wherein the final concentration of the fresh probiotics applied to the consumable product is $10^7$ to $10^8$ cfu/g with respect to the total weight of the consumable product.

47. The method according to claim 11, wherein the final concentration of the fresh probiotics applied to the consumable product is 2 to $8 \times 10^7$ cfu/g with respect to the total weight of the consumable product.

* * * * *